United States Patent [19]
Müller et al.

[11] Patent Number: 5,929,279
[45] Date of Patent: Jul. 27, 1999

[54] PREPARATION OF BISOXIMES

[75] Inventors: Ruth Müller, Friedelsheim; Remy Benoit, Neustadt; Herbert Bayer, Mannheim; Norbert Götz, Worms; Hubert Sauter, Mannheim, all of Germany

[73] Assignee: BASF Aktiengesellschaft, Ludwigshafen, Germany

[21] Appl. No.: 08/930,635

[22] PCT Filed: Mar. 25, 1996

[86] PCT No.: PCT/EP96/01306

§ 371 Date: Oct. 7, 1997

§ 102(e) Date: Oct. 7, 1997

[87] PCT Pub. No.: WO96/32373

PCT Pub. Date: Oct. 17, 1996

[30] Foreign Application Priority Data

Apr. 8, 1995 [DE] Germany ............................ 19513388

[51] Int. Cl.⁶ .................................................. C07C 249/12
[52] U.S. Cl. ...................... 564/256; 548/243; 548/370.1; 558/354; 564/253; 564/254; 564/257
[58] Field of Search ..................................... 564/253, 254, 564/256, 257; 548/243, 370.1; 558/354

[56] References Cited

U.S. PATENT DOCUMENTS

| | | | |
|---|---|---|---|
| 4,158,015 | 6/1979 | Paul | 260/566 A |
| 4,240,981 | 12/1980 | Kok | 564/259 |
| 5,130,486 | 7/1992 | Kongo et al. | 564/256 |

FOREIGN PATENT DOCUMENTS

| | | |
|---|---|---|
| 2908688 | 3/1979 | Germany . |
| 4441674 | 11/1994 | Germany . |
| 95/18789 | 7/1995 | WIPO . |
| 95/21153 | 8/1995 | WIPO . |
| 95/21154 | 8/1995 | WIPO . |
| 95/21156 | 8/1995 | WIPO . |
| 96/07633 | 3/1996 | WIPO . |

OTHER PUBLICATIONS

Hauser et al., J. Org. Chem., vol. 20, 1955 pp. 1491–1495.
J. Gen. Chem., USSR, 58(1), pp. 181–184 (1988).
Tetrahedron, 41/22, 5181, 1985.
J. Org. Chem., USSR, 20, 135 (1984).
J. Org. Chem., USSR 27/1, 97 (1991).
J. Phys. Chem., 91/26, 6490, (1987).
Recl. Trav. Chim. Pays–Bas, 111/2, 79 (1992).
Synth. Rea. Inorg. Met.–Org. Chem., 18(10), 975, (1988).
Z. Anorg. Allg. Chem., 496, 197, 1983.
Synth. Rea. Inorg. Met.–Org. Chem., 11 (7), 621, (1981).
Spectrosc. Lett., 23(6), 713, 1990.

*Primary Examiner*—Peter O'Sullivan
*Attorney, Agent, or Firm*—Keil & Weinkauf

[57] ABSTRACT

A process for the preparation of largely isomerically pure α-bisoximes of the formula Ia $$R^1O\!-\!N\!=\!CR^2\!-\!CR^3\!=\!N\!-\!OR^4 \qquad \text{Ia}$$

where the groups $R^1O$— and $R^2$ on the $N\!=\!C$ bond are cis to one another and where the radicals have the following meanings:

$R^1$ and $R^4$ are hydrogen or a C-organic radical;

$R^2$ is hydrogen, cyano, nitro, hydroxyl, amino, halogen or an organic radical which can be bonded to the structure directly or via an oxygen, sulfur or nitrogen atom;

$R^3$ is hydrogen, cyano, nitro, hydroxyl, amino, halogen, alkyl, haloalkyl, alkoxy, haloalkoxy, alkylthio, alkylamino, dialkylamino or cycloalkyl, from a mixture of the isomers of the a-bisoximes Ia and Ib

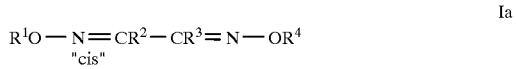
"cis"    Ia

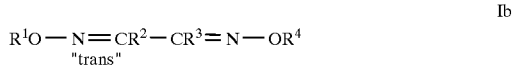
"trans"  Ib is described.

10 Claims, No Drawings

PREPARATION OF BISOXIMES

The present invention relates to a process for the preparation of largely-isomerically pure α-bisoximes of the formula Ia

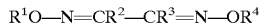

where the groups $R^1O$— and $R^2$ on the N=C bond are cis to one another and where the radicals have the following meanings:

$R^1$ and $R^4$ are hydrogen or a C-organic radical;
$R^2$ is hydrogen, cyano, nitro, hydroxyl, amino, halogen or an organic radical which can be bonded to the structure directly or via an oxygen, sulfur or nitrogen atom;
$R^3$ is hydrogen, cyano, nitro, hydroxyl, amino, halogen, alkyl, haloalkyl, alkoxy, haloalkoxy, alkylthio, alkylamino, dialkylamino or cycloalkyl.

α-Bisoximes are disclosed in the literature as intermediates and as active compounds for the control of animal pests or harmful fungi (WO-A 95/18,789; WO-A 95/21,153; WO-A 95/21,154; WO-A 95/21,156; DE Appl. No. P 44 32 336.0; DE Appl. No. P 44 41 674.1).

Depending on the configuration of the double bond of the group $R^1O$—N=$CR^2$—, the active compounds described in general display different activity, the activity of those compounds customarily being higher in which the groups $R^1O$— and $R^2$ on the N=C bond are cis to one another. Taking this into account, it is proposed in the literature cited to separate the isomers from one another in conventional ways (eg. by chromatography). The separation of the desired isomer from a mixture of isomers has the disadvantage that a not inconsiderable part of expensive intermediates or final products remains unused because they are present in the wrong configuration.

The literature proposes processes for the isomerization of α-bisoximes, whose disadvantage is based on the fact that they are either restricted to oximes having specific (stable) radicals and/or proceed nonselectively and/or only with poor yields [DE-A 29 ar 688; J. General Chem. USSR 58/1 (1988), 181; Tetrahedron 41/22 (1985), 5181; J. Org. Chem. USSR 20 (1984), 135; J. Org. Chem. USSR 27/1 (1991), 97; J. Phys. Chem. 91/26 (1987), 6490; Recl. Trav. Chim. Pays-Bas 111/2 (1992), 79].

The literature additionally describes the conversion of bisoximes into a specific isomer with acid catalysis [Synth. Reakt. Inorg. Met.-Org. Chem. 18(10) (1988), 975; Synth. Reakt. Inorg. Met.-Org. Chem. 11(7) (1981), 621; Spectrosc. Lett. 23(6) (1990), 713; Z. Anorg. Allg. Chem. 496 (1983), 197]. These processes, however, have the disadvantage that they can only be used with those compounds whose substituents are stable to acids.

In addition, the earlier application WO-A 95/21,153 describes the isomerization of the compound A to A' in ether with HCl in 75% yield.

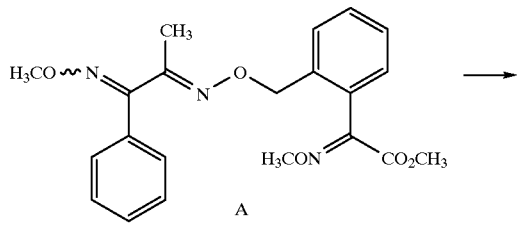

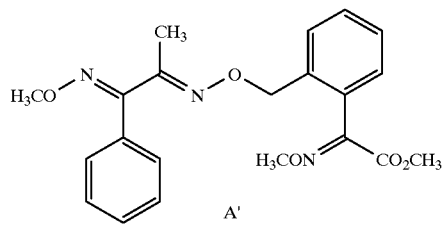

It is an object of the present invention to provide a generally applicable process for the preparation of largely isomerically pure α-bisoximes of the formula Ia

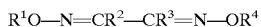

where the groups $R^1O$— and $R^2$ on the N=C bond are cis to one another, which is particularly applicable to those compounds in which the substituents $R^1$, $R^2$, $R^3$ and $R^4$ are not stable to acids or contain groups which are not stable to acids.

We have found that this object is achieved by a process for the preparation of largely isomerically pure α-bisoximes of the formula Ia

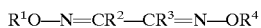

where the groups $R^1O$— and $R^2$ on the N=C bond are cis to one another, which comprises treating a mixture of the isomers of the α-bisoximes Ia and Ib

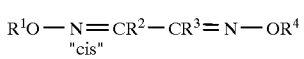

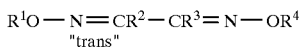

with a Lewis acid in an organic solvent.

The largely isomerically pure α-bisoximes of the formula Ia can also be obtained by the process according to the invention if an α-bisoxime Ib in which the groups $R^1O$— and $R^2$ on the N=C bond are trans to one another is treated with a Lewis acid in an organic solvent.

Fundamentally, the process according to the invention can be carried out in all organic solvents or diluents which do not liberate protic acids with the Lewis acids used. Accordingly, aprotic organic solvents are preferably used.

Suitable solvents are, for example, aliphatic hydrocarbons such as pentane, hexane, heptane, cyclohexane and petroleum ether, aromatic hydrocarbons such as benzene, toluene, o-, m- and p-xylene, halogenated hydrocarbons such as methylene chloride, chloroform, 1,2-dichloroethane and chlorobenzene, ethers such as diethyl ether, diisopropyl ether, tert-butyl methyl ether, dioxane, anisole and tetrahydrofuran, and also dimethyl sulfoxide and dimethylformamide, particularly preferably aliphatic hydrocarbons such as pentane, hexane, heptane, cyclohexane and petroleum ether and aromatic hydrocarbons such as toluene and o-, m- and p-xylene. Mixtures of the solvents mentioned can also be used.

The reaction temperature is dependent on the nature of the substituents of the α-bisoximes. In general, the isomerisation is carried out at at least −40° C. At temperatures of above 150° C., a temperature-related decomposition of the bisoximes may even occur. This temperature-related decomposition depends, however, essentially on the nature and stability of the substituents, so that in cases of stable bisoximes the reaction can also be carried out at higher temperatures.

This reaction is therefore customarily carried out at from −30° C. to 140° C., preferably −10° C. to 120° C.

Fundamentally, in the reaction according to the invention all Lewis acids can be used which are so stable in the selected solvent that no protic acids are released.

Lewis acids which can therefore be used are in general the halides of a semimetal or metal of main group 3 or 4 or of a transition metal. Those preferably used are halides of boron, aluminum, tin, zinc, iron or titanium. Suitable halides in this case are particularly the fluorides, chlorides or bromides. Examples of customary Lewis acids which can be used in the process according to the invention are $AlCl_3$, $AlBr_3$, $FeCl_3$, $BBr_3$, $BCl_3$, $BF_3$, $SnCl_4$, $ZnCl_2$, $ZnBr_2$ or $TiCl_4$.

In general, it is sufficient to use the Lewis acids in catalytic amounts, it being possible for the reaction rate to increase with increasing amount of Lewis acid. Accordingly, amounts of from 0.1 to 500 mol % of the Lewis acid (based on the amount of bisoxime Ib or the mixture of the bisoximes Ia and Ib) are customarily already sufficient. Larger amounts do not interfere with the reaction, but from the economic point of view are in general unnecessary and undesirable with respect to large-scale use of the process (safety aspects and questions of environmental pollution). Accordingly, it is recommended to use the Lewis acids customarily in amounts from 0.5 mol % to 300 mol %, preferably mole to 150 mol %, in particular 10 mol % to 80 mol %.

In accordance with the process measures described above, it is possible, in particular, to prepare largely isomerically pure α-bisoximes of the formula Ia'

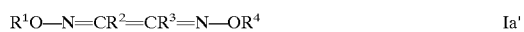

where the groups $R^1O$— and $R^2$ and the groups $R^3$ and —$OR^4$ on the N=C bonds are each cis to one another, by treating a mixture of the isomers of the α-bisoximes Ia' and Ib'

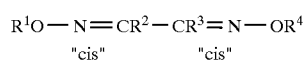

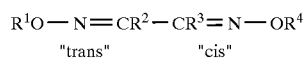

with a Lewis acid in an organic solvent.

The largely isomerically pure α-bisoximes Ia' can also be obtained by the process according to the invention if an α-bisoxime Ib' is treated with a Lewis acid in an organic solvent.

The reaction mixtures are worked up in a customary manner, eg. by mixing with water, separating the phases and, if desired, purifying the crude products by chromatography. The final products are in some cases obtained in the form of viscous oils which are freed from volatile fractions or purified under reduced pressure and at moderately elevated temperature. If the final products are obtained as solids, they can also be purified by recrystallization or digestion.

The process according to the invention is widely applicable. In particular, it is possible by this process to prepare largely isomerically pure a-bisoximes Ia or Ia' which carry groups which are unstable under acidic reaction conditions or which can form complexes with Lewis acids, for example compounds substituted by halogen atoms or ether or ester groups (cf. Table 1).

Unexpectedly, mainly the isomer Ia or Ia' is obtained by the process described above from four possible isomers of the α-bisoximes. The process according to the invention offers reaction conditions under which, in general, preferably an isomerization of the $R^1O$- substituted N=C bond takes place, while an isomerization of the $R^4O$-substituted N=C double bond can largely be avoided {cf. Table 2 and Table 3 ([$i^e$]:$I^x$)}.

It has additionally been shown that the reaction according to the invention is, in particular, also applicable to those α-bisoximes in which $R^1$ and/or $R^4$ is hydrogen.

The process according to the invention is particularly suitable for the preparation of the largely isomerically pure α-bisoximes which are described as intermediates and as active compounds for the control of animal pests or harmful fungi in the literature cited at the outset. Accordingly, the term C-organic radical and the term organic radical in particular comprise the meanings given in general and in particular in this literature.

EXAMPLES

General procedure for the reaction of isomer mixtures of the α-bisoximes a) X mol of the isomer mixture of the α-bisoximes [I'; isomer ratio (Ia':Ib'): $i^o$] in Y ml of the organic solvent ([OS] were treatd with Z mol % of the Lewis acid [LA] and stirred at a temperature [T°C] for t hours. After working up, the isomer ratio [$i^e$] (≡Ia':Ib') obtained under these conditions was investigated by means of gas chromatography (GC), HPLC or $^1$H-NMR spectroscopy (NMR). The results of these investigations are compiled in Table 1.

b) In further experiments, X mol of the isomer mixture of the α-bisoximes I' [$R^1$=$CH_3$, $R^2$=$C_6H_5$, $R^3$=$CH_3$, $R^4$=H; isomer ratio (Ia':Ib'): $i^o$] in Y ml of the organic solvent [OS] were treated with Z mol % of the Lewis acid [LA] and stirred at a temperature [T°C] for t hours. After working up, the isomer ratio [$i^e$]:$I^x$ {[$i^e$]≡Ia':Ib'} obtained under these conditions was investigated by means of gas chromatography (GC), HPLC or $^1$H-NMR spectroscopy (NMR) ($I^x$: amount of a further isomer of still unknown stereochemistry). The results of these investigations are compiled in Table 2.

c) In further experiments according to Z. Anorg. Chem. 496 (1983), 197, X mol of the isomer mixture of the α-bisoximes I' [$R^1$=$CH_3$, $R^2$=$C_6H_5$, $R^3$=$CH_3$, $R^4$=H; isomer ratio (Ia':Ib'): $i^o$] in Y ml of the organic solvent [OS] were saturated with HCl gas and stirred at a temperature [T°C] for t hours. After working up, the isomer ratio [$i^e$]:$I^x$ obtained under these conditions was investigated by means of gas chromatography (GC), HPLC or $^1$H-NMR spectroscopy (NMR) ($I^x$: amount of a further isomer of still unknown stereochemistry; [$i^e$]≡Ia':Ib'). The results of these comparative investigations are compiled in Table 3.

TABLE 1

| No. | R$^1$ | R$^2$ | R$^3$ | R$^4$ | X+ee | i° | Y | OS | Z | LA | T | t | +e,uns i° |
|---|---|---|---|---|---|---|---|---|---|---|---|---|---|
| 01 | CH$_3$ | C$_6$H$_5$ | CH$_3$ | H | 0.208 | 0.7:1 | 200 | toluene | 10 | AlCl$_3$ | 30–40 | 25 | 22.6:1 |
| 02 | CH$_3$ | 4-F—C$_6$H$_4$ | CH$_3$ | H | 0.552 | 0.5:1 | 600 | toluene | 50 | AlCl$_3$ | 60 25 | 9 20 | 9.5:1 |
| 03 | CH$_3$ | 4-Cl—C$_6$H$_4$ | CH$_3$ | H | 0.018 | 0.9:1 | 15 | toluene | 10 | AlCl$_3$ | 25 | 72 | 9.8:1 |
| 04 | CH$_3$ | 3-Cl—C$_6$H$_4$ | CH$_3$ | H | 0.0044 | 1.4:1 | 5 | toluene | 10 | AlCl$_3$ | 25 | 16 | 16.3:1 |
| 05 | CH$_3$ | CH(CH$_3$)$_2$ | CH$_3$ | H | 0.032 | 0.8:1 | 50 | toluene | 10 | AlCl$_3$ | 40 | 9 | 5.4:1 |
| 06 | CH$_3$ | 4-CH$_3$—C$_6$H$_4$ | CH$_3$ | H | 0.024 | 0.8:1 | 100 | toluene | 40 | AlCl$_3$ | 40 | 14 | 8.7:1 |
| 07 | CH$_3$ | 3-CH$_3$-isoxazol-5-yl | CH$_3$ | H | 0.388 | 4:1 | 400 | toluene | 10 | AlCl$_3$ | 30–40 25 | 8 12 | 9:1 |
| 08 | CH$_3$ | 4-CN—C$_6$H$_4$ | CH$_3$ | H | 0.329 | 1.5:1 | 400 | toluene | 10 | AlCl$_3$ | 30–40 25 | 5 72 | 9:1 |
| 09 | CH$_3$ | 3-CN—C$_6$H$_4$ | CH$_3$ | H | 0.37 | 2:1 | 400 | toluene | 10 | AlCl$_3$ | 30–40 25 | 8 16 | 9:1 |
| 10 | CH$_3$ | 3-CH$_3$CH$_2$CH(CH$_3$)-isoxazol-5-yl | CH$_3$ | H | 0.013 | 2.3:1 | 30 | toluene | 40 | AlCl$_3$ | 40–50 25 | 8 16 | 9:1 |
| 11 | Pg* | 4-Cl—C$_6$H$_4$ | CH$_3$ | H | 0.377 | 0.7:1 | 500 | toluene | 40 | AlCl$_3$ | 25 40 | 16 5.5 | 28.7:1 |
| 12 | Pg* | 4-Cl—C$_6$H$_4$ | CH$_3$ | H | 0.377 | 0.9:1 | 500 | toluene | 40 | AlCl$_3$ | 25 40 | 16 5.5 | 38.5:1 |
| 13 | CH$_3$ | 3-(CH$_3$)$_2$CH-isoxazol-5-yl | CH$_3$ | H | 0.401 | 3.1:1 | 100 | toluene | 10 | AlCl$_3$ | 30–40 25 | 8 16 | 10.2:1 |
| 14 | Pg* | 3-(CH$_3$)$_2$CH-isoxazol-5-yl | CH$_3$ | H | 0.015 | 2.6:1 | 100 | toluene | 10 | AlCl$_3$ | 40 25 | 6 16 | 9:1 |

*Pg = CH$_2$C≡CH

TABLE 2

| No. | X+ee | i° | Y | OS | Z | LA | T | t | [+e,uns i°]:I$^x$ |
|---|---|---|---|---|---|---|---|---|---|
| 15 | 0.11 | 0.9:1 | 50 | toluene | 10 | BCl$_3$ | 25 | 22 | [4.4:1]:0.4 |
| 16 | 0.011 | 0.9:1 | 50 | toluene | 10 | BBr$_3$ | 25 | 22 | [9.8:1]:0.5 |
| 17 | 0.011 | 0.9:1 | 20 toluene 3 CH$_2$Cl$_2$ | | 10 | TiCl$_4$ | 30 | 22 | [11.1:1]:0.2 |
| 18 | 0.011 | 0.9:1 | 20 | toluene | 50 | AlCl$_3$ | 25 | 22 | [4.6:1]:0 |
| 19 | 0.011 | 0.9:1 | 50 | toluene | 20 | AlCl$_3$ | 50 | 24 | [7.7:1]:0.2 |
| 20 | 0.011 | 0.8:1 | 15 | CH$_2$Cl$_2$ | 13 | AlCl$_3$ | 25 | 72 | [8.1:1]:0.2 |
| 21 | 0.011 | 0.9:1 | 10 | toluene | 10 | AlCl$_3$ | 40 | 5.5 | [47.2:1]:0.4 |
| 22 | 0.011 | 0.9:1 | 15 | toleune | 10 | AlCl$_3$ | 40 | 22 | [16.5:1]0.2 |
| 23 | 0.011 | 0.8:1 | 15 | THF | 10 | AlCl$_3$ | 25 | 72 | [2:1]:0.2 |
| 24 | 0.011 | 0.9:1 | 50 | toluene | 10 | AlCl$_3$ | 80 | 22 | [5.1:1]:0.5 |

THF = tetrahydrofuran

TABLE 3

| No. | X | i° | Y | OS | T | t | [i°]:I$^x$ |
|---|---|---|---|---|---|---|---|
| A | 0.021 | 0.8:1 | 20 20 | O(C$_2$H$_5$)$_2$ O(C$_2$H$_5$)$_2$ × HCl | 25 | 22 | [3.5:1]:0.8 |
| B | 0.029 | 0.8:1 | 20 50 | CH$_2$Cl$_2$ CH$_2$Cl$_2$ × HCl | 25 | 24 | [4.8:1]:2.5 |

Example 01

(Table 1): Preparation of (E,E)-1-phenyl-1-methoxyiminopropan-2-one-2-oxime 40 g (0.208 mol) of (E,E/Z,E)-1-phenyl-1-methoxyiminopropan-2-one-2-oxime (isomer ratio E,E : Z,E=1:1.4) in 200 ml of toluene were treated with 2.77 g of AlCl$_3$. After 25 h at 30–40° C., the reaction mixture was treated with ethyl acetate. The mixture was washed with 2N hydrochloric acid and dried. The solvent was then distilled off under reduced pressure. After crystallization in n-pentane, 32.5 g (81% of theory) of the title compound were obtained as colorless crystals (m.p.: 160–162° C.).

1H-NMR [CDCl$_3$/TMS; δ (ppm)]: 2.10 (s, 3H); 3.91 (s, 3H); 7.17 (m, 2H); 7.40 (m, 3H); 8.66 (s broad, OH)

Example 02

(Table 1): Preparation of (E,E)-1-(4-fluorophenyl)-1-methoxyiminopropan-2-one-2-oxime 115.9 g (0.552 mol) of (E,E/Z,E)-1-(4-fluorophenyl)-1-methoxyiminopropan-2-one-2-oxime (isomer ratio E,E : Z,E=1:1.9) in 600 ml of toluene were treated with 36.7 g of AlCl$_3$. After 9 h at 60° C. and 20 h at room temperature (about 25° C.), the reaction mixture was added to a mixture of ethyl acetate and ice water. The mixture was treated with 10% strength hydrochloric acid and extracted with ethyl acetate. The organic phase was washed and dried. The solvent was then distilled off under reduced pressure. After crystallization in n-pentane, 86.4 g (75% of theory) of the title compound were obtained as colorless crystals (m.p.: 156–157° C.).

1H-NMR [CDCl$_3$/TMS; δ (ppm)]: 2.10 (s, 3H); 3.91 (s, 3H); 7.03–7.25 (m, 4H); 8.67 (s, OH)

Example 03

(Table 1): Preparation of (E,E)-1-(4-chlorophenyl)-1-methoxyiminopropan-2-one-2-oxime 4 g (0.018 mol) of (E,E/Z,E)-1-(4-chlorophenyl)-1-methoxyiminopropan-2-one-2-oxime (isomer-ratio E,E : z,E=1:1.1) in 15 ml of toluene were treated with 0.2 g of AlCl$_3$. After 72 h at room temperature (about 25° C.), the reaction mixture was treated with ice water. The mixture was extracted with tert-butyl methyl ether. The organic phase was washed with 10% strength hydrochloric acid and water and dried. The solvent was then distilled off under reduced pressure. After crystallization in n-pentane, 3.4 g (85% of theory) of the title compound were obtained as colorless crystals (m.p.: 174–176° C.).

1H-NMR [CDCl$_3$/TMS; δ (ppm)]: 2.13 (s, 3H); 3.92 (.s, 3H); 7.12 (d, 2H); 7.36 (d, 2H); 8.42 (s broad, OH)

Example 07

(Table 1): Preparation of (Z,E)-1-(3-methylisoxazol-5-yl)-1-methoxyiminopropan-2-one-2-oxime 76.4 g (0.388 mol) of (E,E/Z,E)-1-(3-methylisoxazol-5-yl)-1-methoxyiminopropan-2-one-2-oxime (isomer ratio Z,E : E,E=4:1) in 400 ml of toluene were treated with 5.2 g of AlCl$_3$. After 8 h at 30–40° C. and a further 12 h at room temperature (about 25° C.), the reaction mixture was added to a mixture of 100 ml of ethyl acetate and 200 ml of 2N hydrochloric acid. The mixture was extracted with ethyl acetate. The organic phase was washed and dried. The solvent was then distilled off under reduced pressure. After crystallization in n-pentane, 65 g (85% of theory) of the title compound were obtained as yellowish crystals in a purity of 90%.

1H-NMR [CDCl$_3$/TMS; δ (ppm)]: 2.18 (s, 3H); 2.35 (s, 3H); 4.07 (s, 3H); 6.57 (s, 1H); 9.67 (s broad, OH)

Example 08

(Table 1): Preparation of (E,E)-1-(4-cyanophenyl)-1-methoxyiminopropan-2-one-2-oxime 71.4 g (0.329 mol) of (E,E/Z,E)-1-(4-cyanophenyl)-1-methoxyiminopropan-2-one-2-oxime (isomer ratio E,E : Z,E=1.5:1) in 400 ml of toluene were treated with 4.4 g of AlCl$_3$. After 5 h at 35–40° C. and a further 72 h at room temperature (about 25° C.), the reaction mixture was added to a mixture of ethyl acetate and 2N hydrochloric acid. After extraction with ethyl acetate, the organic phase was washed and dried. The solvent was then distilled off under reduced pressure. After crystallization in n-pentane/methanol, 60.6 g (85% of theory) of the title compound were obtained as yellowish crystals (m.p.: 165–170° C.).

1H-NMR [CDCl$_3$/TMS; δ (ppm)]: 2.13 (s, 3H); 3.92 (s, 3H); 7.27 (d, 2H); 7.66 (d, 2H); 8.75 (s broad, OH)

Example 09

(Table 1): Preparation of (E,E)-1-(3-cyanophenyl)-1-methoxyiminopropan-2-one-2-oxime 80.2 g (0.37 mol) of (E,E/Z,E)-1-(3-cyanophenyl)-1-methoxyiminopropan-2-one-2-oxime (isomer ratio E,E : Z,E=2:1) in 400 ml of toluene were treated with 4.9 g of AlCl$_3$. After 8 h at 30–40° C. and a further 16 h at room temperature (about 25° C.), the reaction mixture was added to a mixture of ethyl acetate and 2N hydrochloric acid. After extraction with ethyl acetate, the organic phase was washed and dried. The solvent was then distilled off under reduced pressure. After crystallization in n-pentane/methanol, 67.1 g (84% of theory) of the title compound were obtained as yellowish crystals (m.p.: 163–166° C.).

1H-NMR [CDCl$_3$/TMS; δ (ppm)]: 2.13 (9, 3H); 3.93 (s, 3H); 7.40–7.66 (m, 4H); 8.54 (s broad, OH)

Example 25

Preparation of (E,E/Z,E)-1-phenyl-1-methoxyiminopropan-2-one-2-oxime 100 g (0.614 mol) of 1-phenyl-1,2-propanedione-2E-oxime in 200 ml of methanol and 144 g of pyridine were treated with a solution of 77 g (0.922 mol) of O-methylhydroxylamine hydrochloride and 200 ml of methanol. After 24 h at room temperature (about 25° C.), the solvent was removed under reduced pressure. The residue thus obtained was taken up in tert-butyl methyl ether and treated with 2N hydrochloric acid. The aqueous phase was extracted again with tert-butyl methyl ether. After washing, drying and removing the solvent, the mixture of the isomers E,E:Z,E was obtained from the combined organic phases in a ratio of 1:1.4 (GC determination) in a purity of 90–95%.

1H-NMR [CDCl$_3$/TMS; δ (ppm)]: 2.05/2.10 (2s, 1H,1H*); 3.91/3.97 (2s, 1H,1H*); 7.18/7.38/7.61 (3m, 5H,5H*); 9.14 (s broad, OH,OH*)

It was possible to obtain, for example, the compounds Ia' listed in Table 4 in a similar manner:

TABLE 4

| | I' | | | | | | Solvent | Lewis acid | | of | Yield +e,uns |
|---|---|---|---|---|---|---|---|---|---|---|---|
| No. | R$^1$ | R$^2$ | R$^3$ | R$^4$ | X+ee | i° | Y | OS | Z | LA | T | t | Ia' |
| 26 | Pg* | 4-F—C$_6$H$_4$ | CH$_3$ | H | 0.253 | 0.4:1 | 250 | toluene | 60 | AlCl$_3$ | 25 40 | 30 11 | 64–70% |
| 27 | Pg* | 4-Cl—C$_6$H$_4$ | CH$_3$ | H | 0.377 | 0.8:1 | 500 | toluene | 40 | AlCl$_3$ | 25 40 | 16 5.5 | 78–84% |
| 28 | CH$_3$ | (E)-4-CH$_3$ON=C(CH$_3$)—C$_6$H$_4$ | CH$_3$ | H | 0.021 | 1:1 | 100 | toluene | 30 | AlCl$_3$ | 40 25 | 5 16 | 67% |
| 29 | CH$_3$ | N-(4-Cl—C$_6$H$_4$)-pyrazol-4-yl | CH$_3$ | H | 0.017 | 1:1 | 80 | toluene | 30 | AlCl$_3$ | 40 25 | 6 16 | 76% |

*Pg = CH$_2$C≡CH

We claim:

1. A process for the preparation of α-bisoximes of the formula Ia

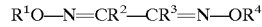     Ia where the groups R$^1$— and R$^2$ on the N=C bond are cis to one another and where the radicals have the following meanings:

R$^1$ is a C-organic radical;

R$^2$ is an organic radical which can be bonded to the structure directly or via an oxygen, sulfur or nitrogen atom;

R$^3$ is hydrogen, cyano, nitro, hydroxyl, amino, halogen, alkyl, haloalkyl, alkoxy, haloalkoxy, alkylthio, alkylamino, dialkylamino or cycloalkyl, and R$^4$ is hydrogen:

which comprises treating a mixture of the isomers of the α-bisoximes Ia and Ib

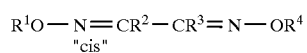

Ia

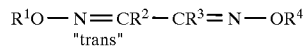

Ib with a Lewis acid in an organic solvent.

2. A process for the preparation of α-bisoximes of the formula Ia as claimed in claim 1, wherein an α-bisoxime Ib as set forth in claim 1, wherein the groups $R^1O$— and $R^2$ on the N=C bond are trans to one another, is treated with a Lewis acid in an aliphatic or aromatic hydrocarbon.

3. A process for the preparation of α-bisoximes of the formula Ia'

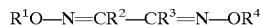 Ia' where the groups $R^1O$— and $R^2$ and the groups $R^3$ and —$OR^4$ on the N=C bonds are each cis to one another as in claim 1, wherein a mixture of the isomers of the α-bisoximes Ia' and Ib'

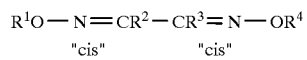 Ia'

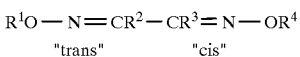 Ib' is treated with a Lewis acid in an aliphatic or aromatic hydrocarbon.

4. A process for the preparation of α-bisoximes of the formula Ia' as claimed in claim 3, wherein an α-bisoxime Ib' as set forth in claim 3, where the groups $R^1O$— and $R^2$ on the N=C bond are trans and the groups $R^3$ and —$OR^4$ on the C=N bond are cis to one another, is treated with a Lewis acid in an organic solvent.

5. A process as claimed in claim 1, wherein the reaction is carried out at from −40° C. to 150° C.

6. A process as claimed in claim 1, wherein the Lewis acid used is a halide of a semimetal or metal of main group 3 or 4 or of a transition metal.

7. A process as claimed in claim 6, wherein the Lewis acid used is a halide of boron, aluminum, tin, zinc, iron or titanium.

8. A process as claimed in claim 6, wherein the halide used is a fluoride, chloride or bromide.

9. A process as claimed in claim 6, wherein the Lewis acid used is a fluoride, chloride or bromide of a semimetal or metal of main group 3 or 4 or of a transition metal.

10. A process as claimed in claim 1, wherein the Lewis acid used is $AlCl_3$, $AlBr_3$, $FeCl_3$, $BBr_3$, $BCl_3$, $BF_3$, $SnCl_4$, $ZnCl_2$, $ZnBr_2$ or $TiCl_4$.

* * * * *

UNITED STATES PATENT AND TRADEMARK OFFICE
CERTIFICATE OF CORRECTION

PATENT NO.: 5,929,279

DATED: July 27, 1999

INVENTOR(S): MUELLER et al.

It is certified that error appears in the above-identified patent and that said Letters Patent is hereby corrected as shown below:

Col. 9, claim 1, line 9 (last line of claim 1), "organic solvent" should be --aliphatic or aromatic hydrocarbon--.

Signed and Sealed this

Thirtieth Day of November, 1999

Attest:

Q. TODD DICKINSON

Attesting Officer

Acting Commissioner of Patents and Trademarks